(12) United States Patent
Colombo et al.

(10) Patent No.: US 7,529,579 B2
(45) Date of Patent: May 5, 2009

(54) METHODS FOR REAL-TIME AUTONOMIC NERVOUS SYSTEM MONITORING USING TOTAL HEART RATE VARIABILITY, AND NOTCHED WINDOWING

(75) Inventors: Joseph Colombo, Richboro, PA (US);
Robert G. Welch, Media, PA (US);
Benhur Aysin, Bensalem, PA (US)

(73) Assignee: Ansar, Inc., Philadelphia, PA (US)

( * ) Notice: Subject to any disclaimer, the term of this patent is extended or adjusted under 35 U.S.C. 154(b) by 581 days.

(21) Appl. No.: 11/178,714

(22) Filed: Jul. 11, 2005

(65) Prior Publication Data

US 2006/0100534 A1 May 11, 2006

Related U.S. Application Data

(60) Provisional application No. 60/586,804, filed on Jul. 9, 2004.

(51) Int. Cl.
*A61B 5/0402* (2006.01)

(52) U.S. Cl. ..................................................... 600/513

(58) Field of Classification Search ................... 600/513
See application file for complete search history.

(56) References Cited

U.S. PATENT DOCUMENTS 6,826,428 B1 * 11/2004 Chen et al. ................... 607/40

* cited by examiner

*Primary Examiner*—Kennedy J Schaetzle
(74) *Attorney, Agent, or Firm*—Fox Rothschild LLP

(57) ABSTRACT

The present invention is a method and apparatus for non-invasive, real-time monitoring of the autonomic nervous systems. The present invention allows for monitoring of the autonomic nervous system using spectral analysis of both heart rate and respiratory signals. A preferred embodiment uses short-time Fourier transform (STFT) with a novel modified Bartlett windowing scheme in real-time so that the dynamic interactions between the sympathetic and parasympathetic divisions of the autonomic nervous system can be independently monitored. In addition, a preferred embodiment of the present invention uses the same techniques to monitor other biological or physiological data, including continuous blood pressure.

5 Claims, 10 Drawing Sheets

$$x_i := \sin\left(\pi \cdot \frac{i}{10}\right), \text{ where } i = 0, 1, \ldots, 63$$

$x_i := \sin\left(\pi \cdot \dfrac{i}{10}\right) + \text{rnd}(1) - .5$, where $i = 0, 1, \ldots, 63$, and 'rnd' is a Gaussian random noise generator.

$x_i := rnd(1)$, where $i = 0, 1, ..., 63$

| Window Type | | LFA | | | RFa | |
|---|---|---|---|---|---|---|
| | Ave | StDev | P | Ave | StDev | P |
| Bartlett | 10 | 33.998 | | 3.328 | 9.8 | |
| Negative-Slope | 10.228 | 31.375 | 0.46995 | 4.859 | 15.143 | 0.09745 |
| Positive-Slope | 10.228 | 31.375 | 0.46995 | 4.859 | 15.143 | 0.09745 |
| Inverted Bartlett | 9.742 | 29.671 | 0.46521 | 4.428 | 18.539 | 0.21147 |
| Rectangular | 29.283 | 78.501 | 0.00031 | 13.662 | 56.036 | 0.00284 |

Figure 20

METHODS FOR REAL-TIME AUTONOMIC NERVOUS SYSTEM MONITORING USING TOTAL HEART RATE VARIABILITY, AND NOTCHED WINDOWING

CROSS-REFERENCE TO RELATED APPLICATIONS

This application is based on and claims priority to U.S. Provisional Application No. 60/586,804, filed Jul. 9, 2004, incorporated fully herein by reference.

BACKGROUND OF THE INVENTION

Field of the Invention

The present invention relates, in general, to systems for monitoring the autonomic nervous system, and more specifically to a system for using real-time heart rate spectral analysis for monitoring the autonomic nervous system.

The autonomic nervous system regulates involuntary functions of nearly all parts of the body in health and disease. It is comprised of two main subdivisions known as the sympathetic nervous system (sympathetic system) and the parasympathetic nervous system (parasympathetic system). The sympathetic system is the system that helps the body respond to stressful situations, and is often referred to as the "fight or flight" system. For example, under stressful conditions the sympathetic system increases the rate in which neurons are fired in order to increase the heart rate, elevate blood pressure, and slow down the digestive process. In contrast, the parasympathetic system helps the body preserve and restore energy. It is often referred to as the "rest and digest" system. For example, when one relaxes by resting in a chair, the parasympathetic system slows the heart, lowers blood pressure, and speeds the digestive process.

Under normal resting or sleeping conditions, the parasympathetic system is dominant. The sympathetic system normally predominates during wakeful periods or with the addition of external stressful conditions. However, certain conditions such as chronic stress, disease, and emotion, can alter the natural balance between the parasympathetic system and the sympathetic system. These factors generally create a persistent elevation in activity in the sympathetic system and a reduction in activity in the parasympathetic system or vise versa. If not controlled, such an imbalance in the autonomous nervous system can impair the functioning of many organs including the heart, vasculature, endocrine system, gastrointestinal (GI) track, kidneys, and lungs. Such impairment can lead to conditions such as altered blood pressure, heart disease, vascular disease, hormone imbalance, GI track immobility, kidney failure and electrolyte imbalance, and other organ related conditions.

Today, medications are available that regulate the autonomic nervous system, such as ACE-inhibitors, beta-blockers, vasopressors, and anti-depressants. These medicines are used to treat altered blood pressure, irregular heart rhythm, chronic fatigue, diabetes, orthostasis, depression, and other conditions related to the autonomic nervous system. These medicines affect the synthesis, release, uptake, and re-uptake of the body's neural chemistry by acting on the receptors in neurons or muscles located in the various areas of the body, such as the brain, heart, kidney, and blood vessels. Many patients use several of these medications simultaneously; thus, it is increasingly important to be able to measure the response of the autonomic nervous system to ensure that the medications are having the desired effects and that a combination of medications is not creating an undesirable imbalance in the autonomic system.

Injury, lifestyle, and disease can also have an affect on the autonomic nervous system. For example, diabetes often leads to a condition known as Diabetic Autonomic Neuropathy, which is a condition whereby there is damage to the autonomic nerves. This, in turn, can lead to poor peripheral blood flow, GI track immobility, sexual dysfunction, kidney disease, blindness and silent myocardial ischemia. Silent myocardial ischemia is a condition whereby the patient experiences episodes of blood flow constriction to the heart muscle that is often unnoticed because of an absence of chest pain due to a concurrent loss of sensory neurons. Conditions such as these require that the autonomic nervous system be closely and accurately monitored.

An effective method to monitor the autonomic nervous system is to monitor the function of the heart and the lungs and use the information gathered to derive information regarding the autonomic nervous system. In other words, the heart and lungs together can be used as a "window" through which it is possible to study the activity of the autonomic nervous system. Heart rate is equal to the number of heartbeats occurring within a specific length of time, and is normally measured in beats per minute (bpm). For example, increases in heart rate, including to above 100 bpm (known as tachycardia), are generally considered to result from activity in the sympathetic system. Decreases in heart rates, including to below 60 bpm (known as bradycardia), are generally considered to result from the activity in the parasympathetic system.

However, because the heart rate is influenced over time by both the sympathetic and parasympathetic systems, the average or mean heart rate is a poor indicator for monitoring the state of balance within the autonomic nervous system. A better picture can be derived using the instantaneous heart rate. The instantaneous heart rate can be determined by measuring the time interval between two heartbeats using a standard electrocardiogram (EKG). An accelerating heart rate will exhibit a decreasing time interval between beats, while a decelerating heart rate will exhibit an increasing time interval between beats. By measuring spontaneous changes in heart rate, the autonomic nervous system can be monitored more accurately. The parasympathetic system can cause a very fast response, capable of being observed on the next heartbeat (1 to 3 seconds), while response to sympathetic system activity is typically slower, often taking three to five heart beats (10 to 20 seconds). This makes it possible to distinguish activity within the two systems by observing the characteristics of the heart rhythm using frequency-domain analysis, which is well known in the art.

Recently two forms of spectral analysis of real-time HRV have been introduced into the medical market place. One such embodiment is based on a fast Fourier transform (FFT) spectral analysis technique and the other embodiment was based on the continuous wavelet transform (CWT) spectral analysis technique. Although CWT based spectral analysis techniques are more suitable for nonstationary structure of heart rate fluctuations, FFT based methods are shown to provide good results for critical care patients where patients lay down in a bed motionless. For those patients data is very consistent or almost stationary since they are motionless. Therefore FFT based methods tend to give better results.

SUMMARY OF THE INVENTION

The present invention is a method and apparatus for non-invasive, real-time monitoring of the autonomic nervous systems. The present invention allows for monitoring of the autonomic nervous system using spectral analysis of both heart rate and respiratory signals.

A preferred embodiment uses short-time Fourier transform (STFT) with a novel modified Bartlett windowing scheme in real-time so that the dynamic interactions between the sympathetic and parasympathetic divisions of the autonomic nervous system can be independently monitored. In addition, a preferred embodiment of the present invention uses the same techniques to monitor other biological or physiological data, including continuous blood pressure.

The present invention applies the technique of STFT with the special windowing scheme to process signals obtained from various physiological sensors. Segments of the signal are first windowed and then Fourier transform is applied. The processed input signals provide a frequency domain output of the instantaneous heart rate and respiration.

BRIEF DESCRIPTION OF THE DRAWINGS

FIG. 20 is a table presenting the summary analyses of window variant comparisons.

DETAILED DESCRIPTION OF THE PREFERRED EMBODIMENTS

The preferred embodiment of the present invention provides a method and apparatus for autonomic nervous system monitoring. Inputs from two sources (ECG and impedance plethsymography (respiration) sources) are obtained and processed using STFT analysis with a modified Bartlett windowing scheme, described in more detail below. The results of the processing are displayed at an output (e.g., a video monitor). It is understood that while the preferred embodiment described herein uses EKG and impedance plethsymography as the input sources, other input source may be used and still fall within the scope of the present invention.

Figure 1:
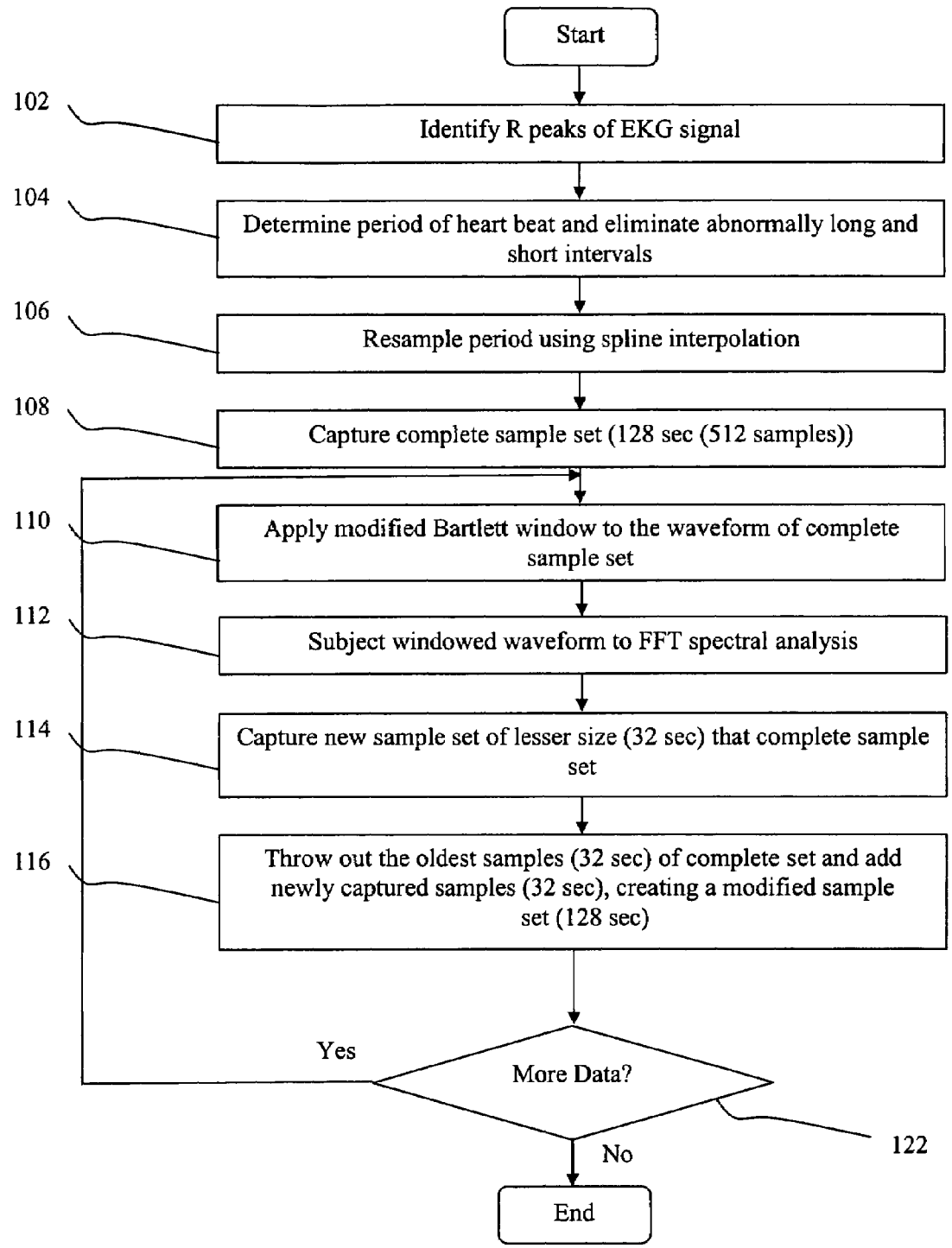
FIG. 1 is a flowchart which illustrates the basic steps of the technique of the present invention.

FIG. 1 illustrates the basic steps of the technique of the present invention. The first step in conducting a heart rate analysis in accordance with the present invention is to identify R peaks of the EKG signal (Step 102). The R peak of the wave is detected according to FDA approved methods well known in the art. The R-peak corresponds to the point of maximum ventricular depolarization. This nomenclature is well known in the art. Next, the period of the heartbeat is determined (Step 104). The time between the onset of one heartbeat (P peak) and the onset of the next heartbeat represents the period of the heart. However, because the R peak is more easily identified than the P peak, and the P-R interval is relatively constant, the generally accepted practice is to use the time interval between two consecutive R peaks as the measure of the heart period. To identify the R peaks, the EKG signal is first filtered using a band-pass filter to reduce noise that could distort the wave. The R peaks are then identified using a differentiation and threshold algorithm to produce a pulse train, from which it is possible to identify when the derivative exceeds a set threshold. Once the R peaks are identified, the time interval between the peaks can be computed by using the pulse train to start and reset a clock. Any abnormally short and long intervals are also eliminated to provide normal RR intervals. The result is a sequence of R-R durations known in the art as the RR-interval tachogram.

Then the RR interval is re-sampled using the spline interpolation (Step 106). This assures that any subsequent spectral analysis is performed on an evenly sampled, discrete time signal as opposed to the original unevenly sampled R-R interval tachogram. In some embodiments, it is desired to convert the measurement of R-R intervals (heart period) into an instantaneous heart rate, expressed in bpm. This is accomplished by using the following relationship: Heart rate=60/heart period.

The preferred embodiment of the STFT technique includes capturing 512 samples (128 seconds; sampling rate is 4 Hz) of approximately stable, non-stationary, instantaneous Heart Rate (IHR) and Respiratory Activity (RA) data (Step 108), independently applying a modified Bartlett window to each of these waveforms (Step 110), and passing the resulting windowed data, each independently, through an FFT spectral analysis software program in a computer microprocessor (Step 112). It is understood that any method of performing FFT spectral analysis on the resulting windowed data can be used. Then the next 128 Samples (32 seconds) worth of data from the IHR and the RA data are captured (Step 114). The oldest 32 seconds worth of IHR and RA data are omitted while admitting a new 32 seconds worth of new data in a first in, first out (FIFO) methodology (Step 116). This creates a new set of 512 samples with 128 new and 384 old samples for each signal (IHR and RA). The two sets of 512 samples worth of data are each then again windowed and processed through the FFT analyzer. The overall process is then repeated until the data are exhausted (Step 122). By invoking the FFT, data stationarity is called into question; therefore, this technique is better suited for short time or stable continuous baseline monitoring of patients in the critical care setting. Short time or stable continuous monitoring situations include the trauma ward or emergency department (ED), the intensive care unit (ICU); the cardiac care unit (CCU); neonate intensive care unit (NICU); pre-OP, post-OP or the post anesthesia care unit (PACU); and in the operating room (OR) where, due to the patient's condition, the patient is not changing metabolic levels very rapidly.

The preferred embodiment is an FFT analysis technique that includes an analysis window with a wave form that is 0 for all time values up to the beginning of the window, that instantaneously becomes 1 at the beginning of the window, and then linearly decreasing from 1 to 0 by the midpoint of the window (i.e., over the first 64 seconds) and linearly increasing from 0 to 1 by the end of the window (i.e., over the last 64 seconds). At 128 seconds the window transitions instantaneously from 1 back down to 0 and remains 0 through all values in the future. In other words, it is the inverse of a Bartlett window, as given by $$w_{nt}(n) = 1 - w_b(n) \quad 0 \leq n < 512$$

where $w_{nt}(n)$ is the notched window and $w_b(n)$ is a Bartlett window.

This window however, can be linearly scaled to any size and applied to any samples that are to be analyzed in the spectral domain using any form of spectral analyzer that requires windowing including FFT's, and short-time FFT's for example.

Applicant conducted comparisons between the present invention and both its own CWT technique (referred to herein as "Applicant's CWT technique"), disclosed and claimed in co-pending U.S. application Ser. No. 10/387,070 filed on Mar. 12, 2003, and traditional methods. The results are discussed below.

The preferred embodiment of the Applicant's CWT technique has application in real-time so that the dynamic interactions between the sympathetic and parasympathetic divisions of the autonomic nervous system can be independently monitored in the frequency domain. The method in accordance with Applicant's CWT technique allows spectral analysis, formerly limited to the study of stationary data, to be applied to time-varying biological data such as HRV and RA data in the clinical setting. In addition, the Applicant's CWT technique uses the same techniques to monitor other biological or physiological data, including continuous blood pressure.

The preferred embodiment of the Applicant's CWT technique includes capturing 2 minutes samples of IHR and RA activity, and passing the sample data to a CWT software program on a microprocessor. IHR and RA data are updated every 4 seconds. CWT software uses normalized CMORL wavelets with a Q=5 (cycles). Since data stationarity is not an issue with wavelets, the wavelets seem to be better suited to the 15 minute, 6-phase clinical exam that challenges the patient's ANS with a baseline, a deep breathing parasympathetic challenge, a Valsalva sympathetic challenge and a standing postural change systemic autonomic challenge, or the clinical study just looking at postural changes from 5 minute baseline sitting to 5 minutes standing or any other clinical application that requires or desires phases to be 5 minutes or less.

Figure 2:
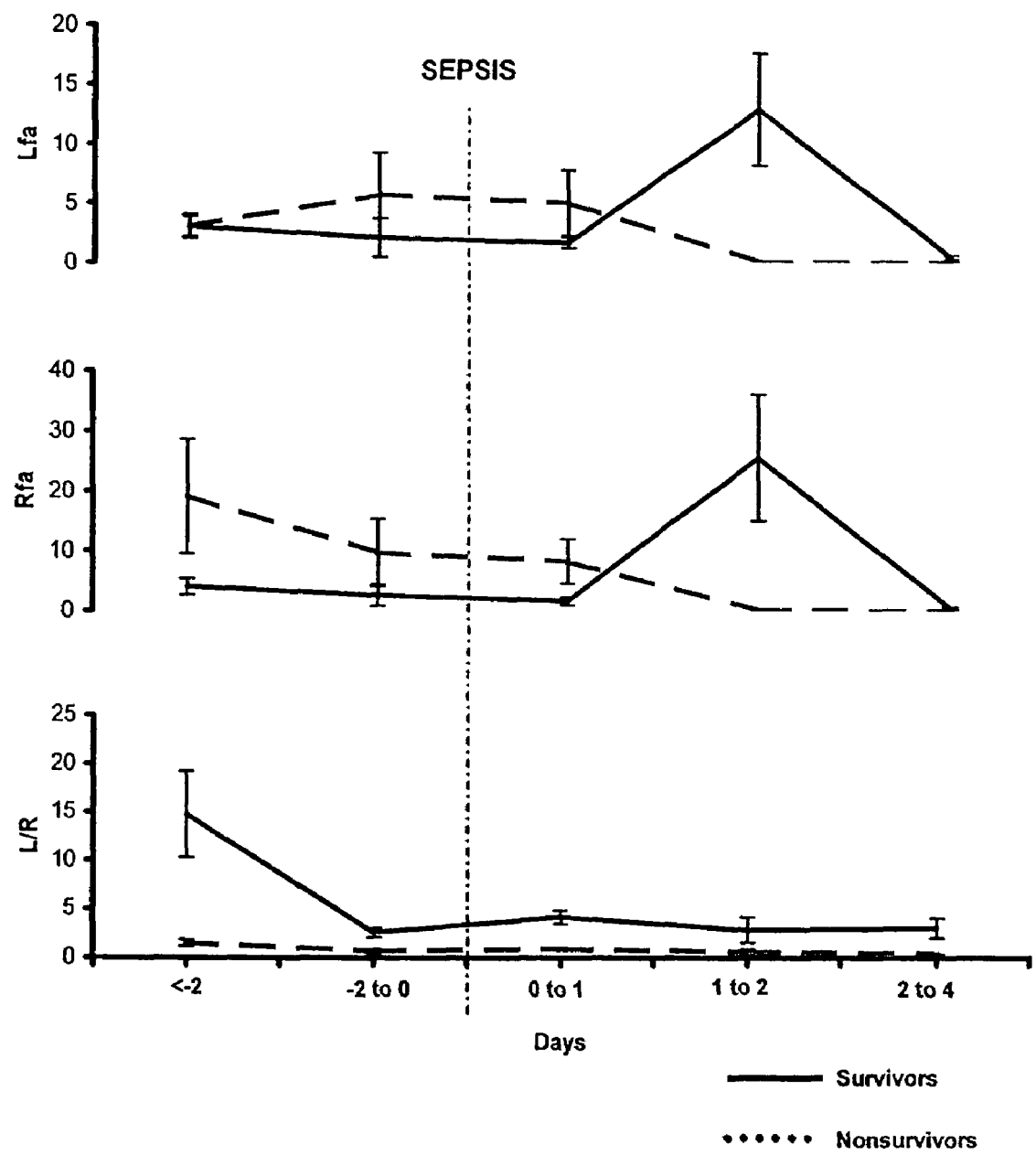
FIG. 2 illustrates low-frequency (LFa: sympathetic), high- or respiratory-frequency (RFa: parasympathetic), and L/R Ratio patterns for survivors and non-survivors of severe sepsis before and after the onset of sepsis, indicated by the vertical dashed line.
Figure 3:
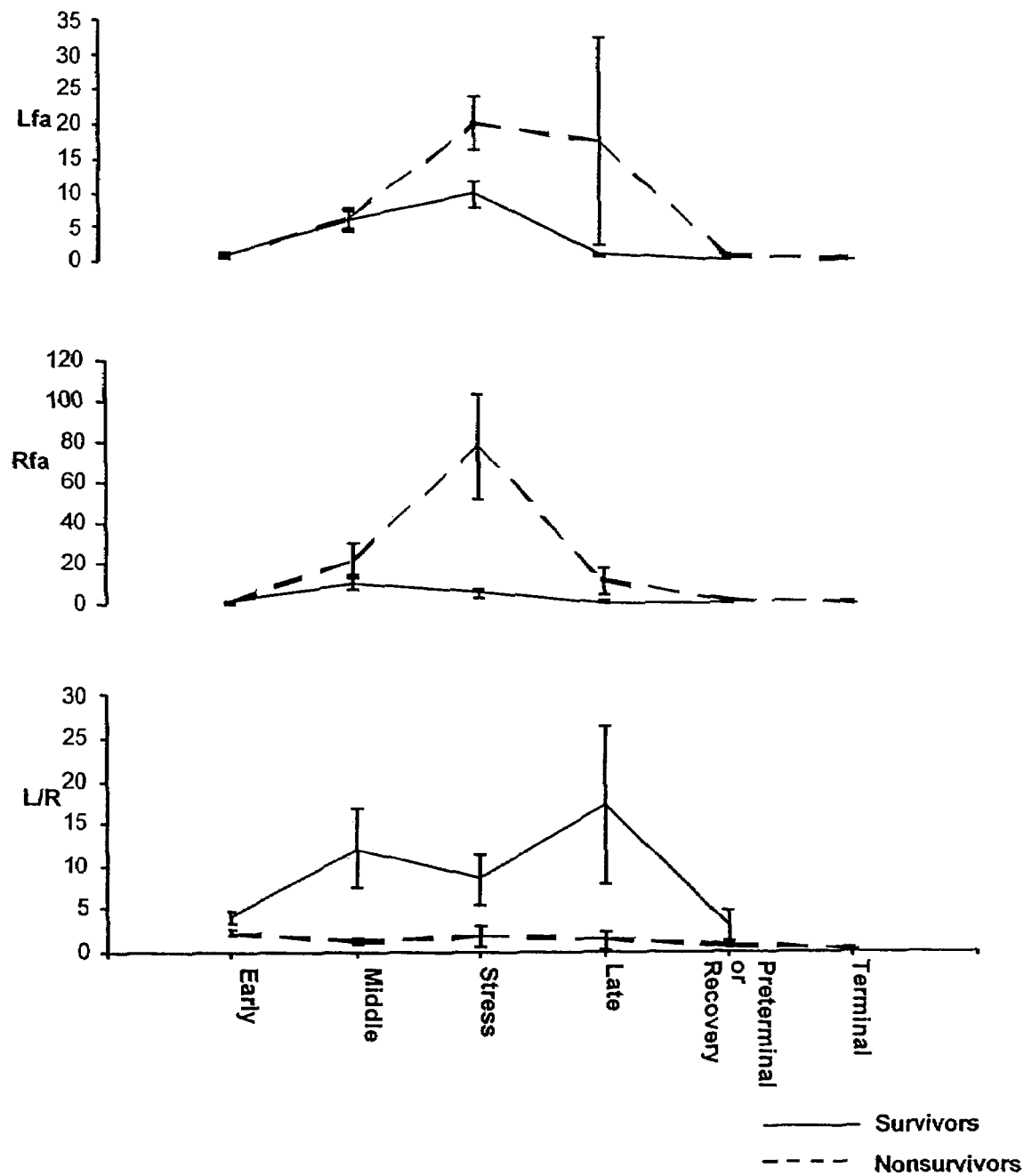
FIG. 3 illustrates low-frequency (LFa: sympathetic), high- or respiratory-frequency (RFa: parasympathetic), and L/R Ratio patterns at post septic various stages for survivors and non-survivors of severe sepsis.
Figure 4:
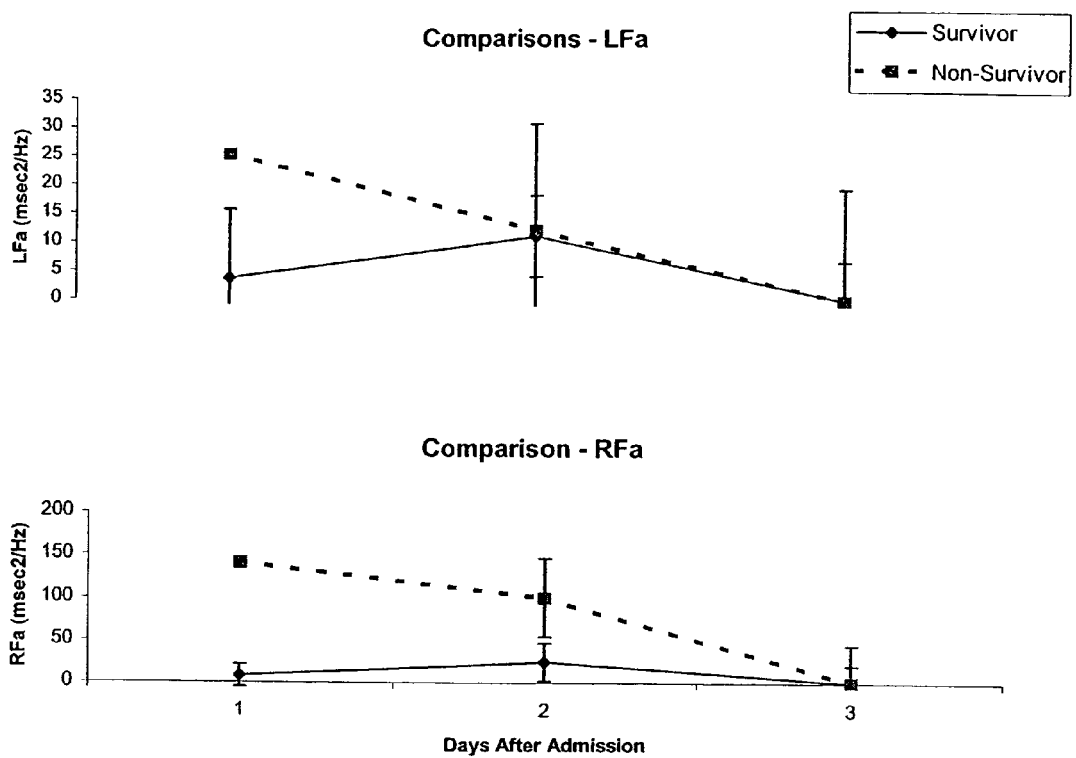
FIG. 4 illustrates sample low-frequency (LFa: sympathetic), high- or respiratory-frequency (FRa: parasympathetic) patterns.

Clinically the preferred embodiments of the two techniques (the present STFT technique of the present invention and Applicant's CWT technique) were compared, using the same set of trauma patients from a level one trauma center at a major city hospital associated with an academic medical institution. It was found that the Applicant's CWT technique was overly sensitive for the acute patient whereas the STFT approach of the present invention provided more stable data that were more meaningful and which correlated well with the patients' outcomes. The meaningful data are presented in FIGS. 2-4. The value and the significance and independence between the two data sets using the STFT approach of the present invention over the that of the Applicant's CWT technique is significant in the prediction of mortality and morbidity in trauma patients and in earlier detection of the onset of sepsis and single or multiple organ failure which hastens the patient's negative end point.

Figure 5:
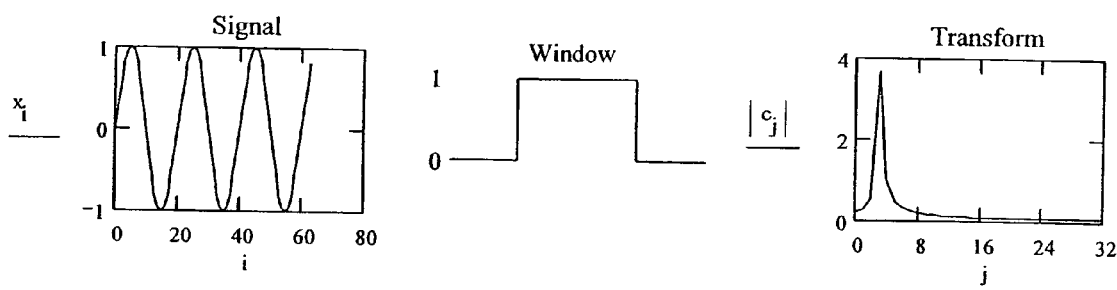
FIG. 5 illustrates a 0.10 Hz sinusoid signal analyzed by a FFT with a square wave window wherein the spectral magnitude is shown on the right and the spectral phase plot is omitted since it does not have any known clinical value.
Figure 6:
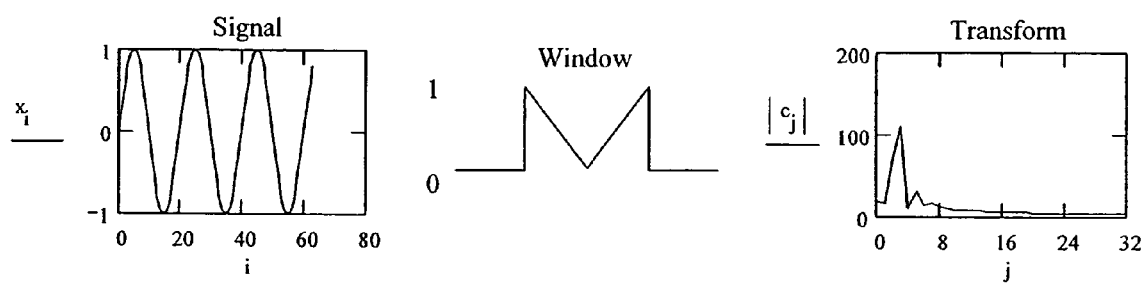
FIG. 6 illustrates a 0.10 Hz sinusoid signal analyzed by an FFT with a notched (or inverted Bartlett) window wherein the spectral magnitude is shown on the right and the spectral phase plot is omitted since it does not have any known clinical value.

Comparison of the STFT Technique of the Present Invention with Traditional methods:

FIG. 5 displays a simulated signal (a 0.01 Hz sinusoid) and its FFT using a rectangular window. FIGS. 6 through 9 depict four variants of a Bartlett window and the spectral responses to a sinusoidal waveform that approximates a healthy patient. FIG. 6 describes the preferred embodiment of the Bartlett window variant. All four variants have very similar spectral magnitude plots, and very different spectral phase plots. However, implementation suggests that the phase plots have no clinical bearing. Note, that the spectrum that results from preferred embodiment (the Bartlett window as shown in FIG. 6 and its inverse naturally, as shown in FIG. 9, includes a low- and high-frequency peak.

Figure 7:
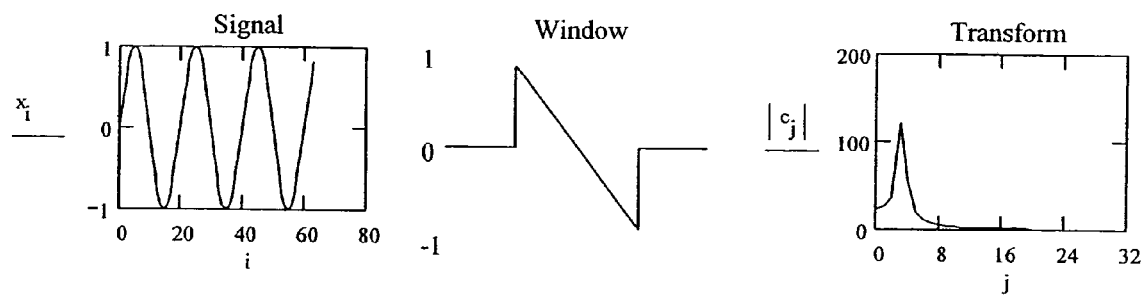
FIG. 7 illustrates a 0.10 Hz sinusoid signal analyzed by an FFT with a negative slope window wherein the spectral magnitude is shown on the right and the spectral phase plot is omitted since it does not have any known clinical value.
Figure 8:
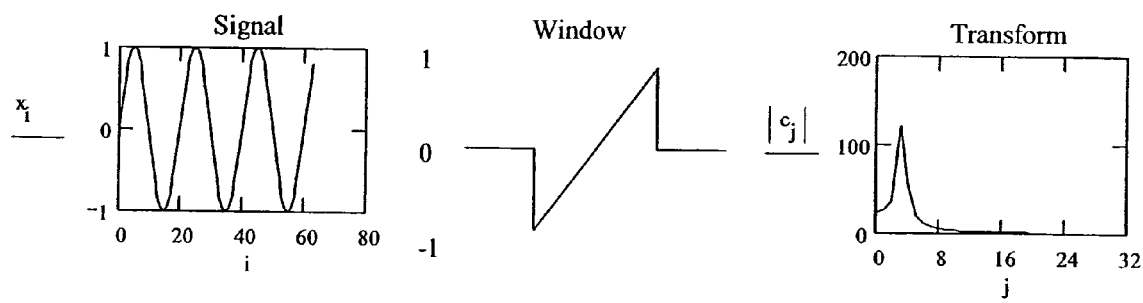
FIG. 8 illustrates a 0.10 Hz sinusoid signal analyzed by an FFT with a positive slope window wherein the spectral magnitude is shown on the right and the spectral phase plot is omitted since it does not have any known clinical value.
Figure 9:
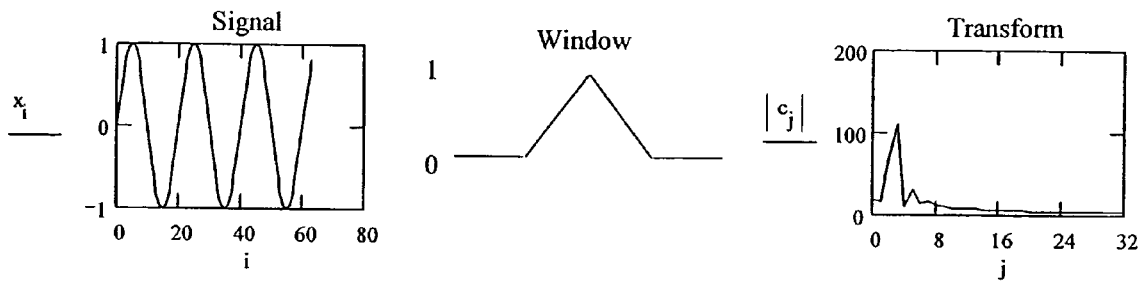
FIG. 9 illustrates a 0.10 Hz sinusoid signal analyzed by an FFT with a Bartlett window wherein the spectral magnitude is shown on the right and the spectral phase plot is omitted since it does not have any known clinical value.
Figure 10:
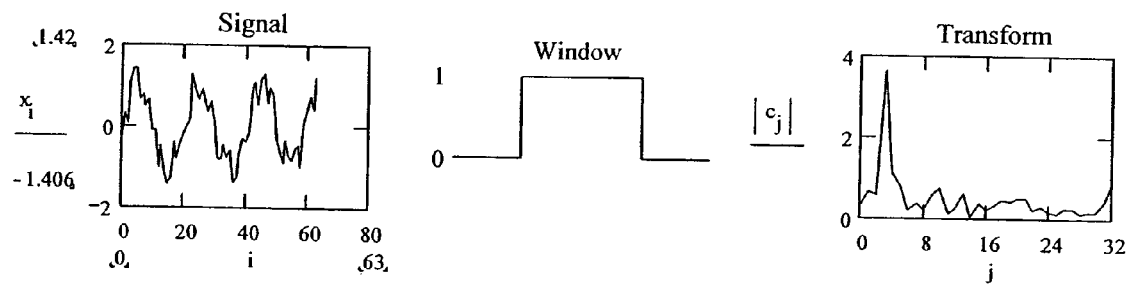
FIG. 10 illustrates a simulated healthy instantaneous heart rate (IHR) signal analyzed by an FFT with a square wave window wherein the spectral magnitude is shown on the right and the spectral phase plot is omitted since it does not have any known clinical value.
Figure 11:
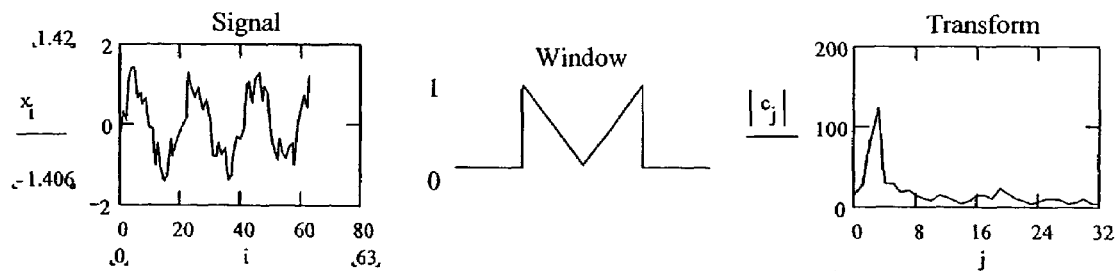
FIG. 11 illustrates a simulated healthy IHR signal analyzed by an FFT with a notched (or inverted Bartlett) window wherein the spectral magnitude is shown on the right and the spectral phase plot is omitted since it does not have any known clinical value.
Figure 12:
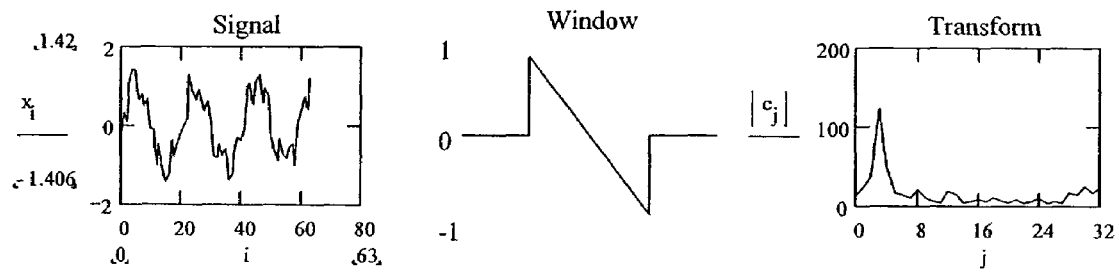
FIG. 12 illustrates a simulated healthy IHR signal analyzed by an FFT with a negative slope window wherein the spectral magnitude is shown on the right and the spectral phase plot is omitted since it does not have any known clinical value.
Figure 13:
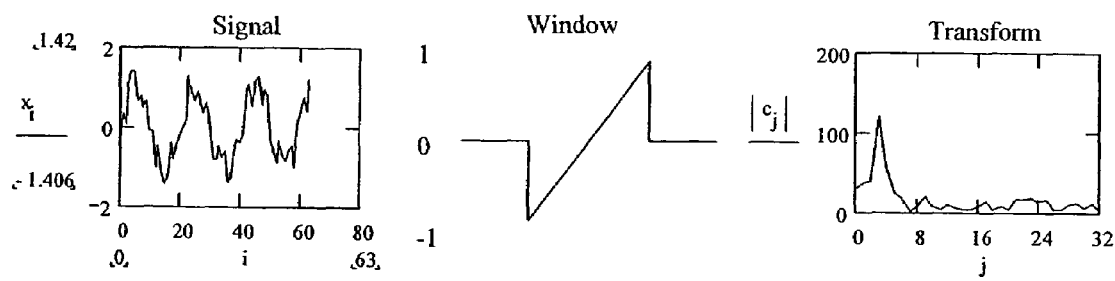
FIG. 13 illustrates a simulated healthy IHR signal analyzed by an FFT with a positive slope window wherein the spectral magnitude is shown on the right and the spectral phase plot is omitted since it does not have any known clinical value.
Figure 14:
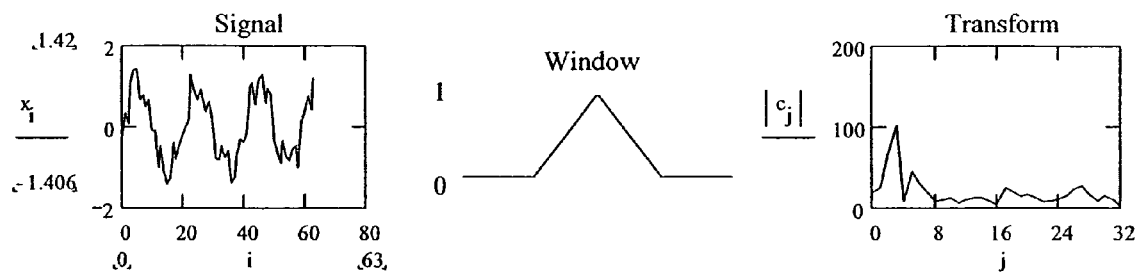
FIG. 14 illustrates a simulated healthy IHR signal analyzed by an FFT with a Bartlett window wherein the spectral magnitude is shown on the right and the spectral phase plot is omitted since it does not have any known clinical value.

FIGS. 7 and 8 display the effects of using the remaining windowing variants on the signal spectra. The windows are negative slope, and positive slope. Only the amplitudes of the spectra are displayed since phase information had no clinical value. FIG. 10 displays a simulated healthy instantaneous heart rate (IHR) signal and its FFT using a rectangular window. FIGS. 11 through 14 depict the Bartlett window and its variants in response to simulated healthy patients (with respiratory sinus arrhythmia).

Figure 15:
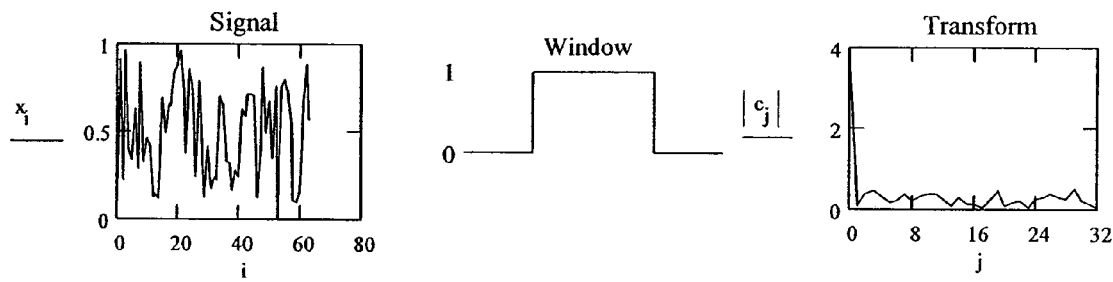
FIG. 15 illustrates a simulated unhealthy (simulated arrhythmic) instantaneous heart rate (IHR) signal analyzed by an FFT with a square wave window wherein the spectral magnitude is shown on the right and the spectral phase plot is omitted since it does not have any known clinical value.
Figure 16:
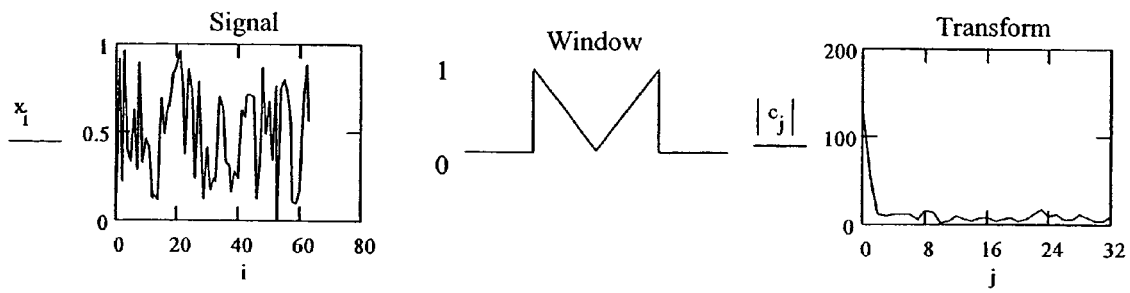
FIG. 16 illustrates a simulated unhealthy (simulated arrhythmic) instantaneous heart rate (IHR) signal analyzed by an FFT with a notched (or inverted Bartlett) window wherein the spectral magnitude is shown on the right and the spectral phase plot is omitted since it does not have any known clinical value.
Figure 17:
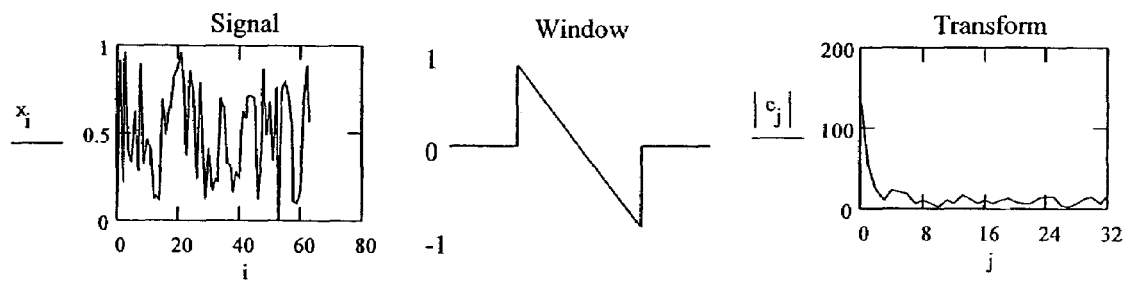
FIG. 17 illustrates a simulated unhealthy (simulated arrhythmic) instantaneous heart rate (IHR) signal analyzed by an FFT with a negative slope window wherein the spectral magnitude is shown on the right and the spectral phase plot is omitted since it does not have any known clinical value.
Figure 18:
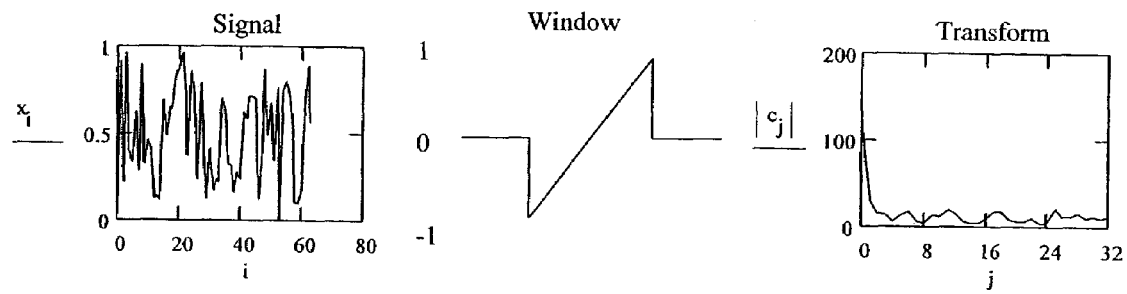
FIG. 18 illustrates a simulated unhealthy (simulated arrhythmic) instantaneous heart rate (IHR) signal analyzed by an FFT with a positive slope window wherein the spectral magnitude is shown on the right and the spectral phase plot is omitted since it does not have any known clinical value.
Figure 19:
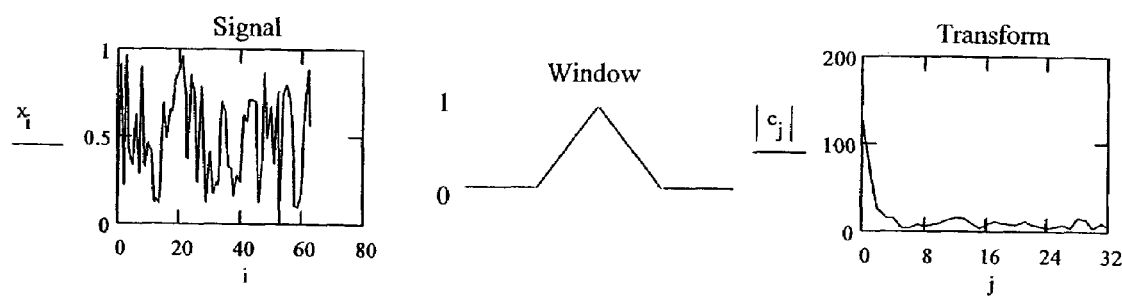
FIG. 19 illustrates a simulated unhealthy (simulated arrhythmic) instantaneous heart rate (IHR) signal analyzed by an FFT with a Bartlett window wherein the spectral magnitude is shown on the right and the spectral phase plot is omitted since it does not have any known clinical value.

FIG. 15 displays a simulated unhealthy instantaneous heart rate (IHR) signal and its FFT using a rectangular window. FIGS. 16 through 19 depict the Bartlett window and its variants in response to simulated unhealthy (simulated arrhythmic) patients. The windowing techniques were then applied to a large sample of clinical data that statistically covers the scope of heart rates and heart rate variabilities that defines the patient population.

FIG. 20 is a table presenting the summary analyses and compares the Bartlett and Bartlett variants to each other and to the rectangular window. The P value for the Bartlett window is computed by comparing it with the standard rectangular window. The P values for the reset are compared to the Bartlett window. The results indicate that the Bartlett window (the notched window), the negative slope window, the positive slope window, and the inverted Bartlett window have statistically similar results, with the negative slope and the positive slope window results identical. The results indicate that for clinical applications the magnitudes of the Bartlett window, the Negative slope window, the Positive slope window, and the inverted Bartlett window have statistically similar results; with the Negative and Positive slope window results identical, and that these windows are statistically different from the rectangular window. From clinical implementation trials, the preferred embodiment has been validated and shown to non-invasively detect earlier the physiologic changes that indicate sepsis and other life-threatening diseases or disorders that adversely impact outcomes.

The above-described steps can be implemented using standard well-known programming techniques. The novelty of the above-described embodiment lies not in the specific programming techniques but in the use of the steps described to achieve the described results. Software programming code which embodies the present invention is typically stored in permanent storage of some type. In a client/server environment, such software programming code may be stored with storage associated with a server. The software programming code may be embodied on any of a variety of known media for use with a data processing system, such as a diskette, or hard drive, or CD-ROM. The code may be distributed on such media, or may be distributed to users from the memory or storage of one computer system over a network of some type to other computer systems for use by users of such other systems. The techniques and methods for embodying software program code on physical media and/or distributing software code via networks are well known and will not be further discussed herein.

It will be understood that each element of the illustrations, and combinations of elements in the illustrations, can be implemented by general and/or special purpose hardware-based systems that perform the specified functions or steps, or by combinations of general and/or special-purpose hardware and computer instructions.

These program instructions may be provided to a processor to produce a machine, such that the instructions that execute on the processor create means for implementing the functions specified in the illustrations. The computer program instructions may be executed by a processor to cause a series of operational steps to be performed by the processor to produce a computer-implemented process such that the instructions that execute on the processor provide steps for implementing the functions specified in the illustrations.

Although the present invention has been described with respect to a specific preferred embodiment thereof, various changes and modifications may be suggested to one skilled in the art and it is intended that the present invention encompass such changes and modifications as fall within the scope of the appended claims.

What is claimed is:

1. A method for power spectral analysis of heart rate variability comprising the steps of:
    capturing a sample set of spline-interpolated heartbeat EKG signals;
    applying a modified Bartlett window to a waveform of the captured sample set;
    subjecting the windowed waveform to short-time Fourier transform (STFT); and
    isolating a respiratory frequency area (RFA) from a low frequency area (LFA).

2. A method as set forth in claim 1, in which said short-time Fourier transform step comprises clinically suppressing mid-range heart rate variability frequencies and accentuating the low-and high-heart rate variability frequency ranges.

3. A method as set forth in claim 2, in which said step to clinically suppress comprises separating and isolating the parasympathetic and sympathetic frequencies of autonomic nervous system function; thereby providing independent, non-invasive, repeatable, digital measures of parasympathetic and sympathetic activity levels.

4. A method as set forth in claim 2, in which said step to clinically suppress comprises monitoring parasympathetic and sympathetic activity to detect the early onset of sepsis, organ failure, and acute respiratory distress syndrome and other life threatening acute and critical care diseases.

5. A method as set forth in claim 2, in which said step to clinically suppress comprises monitoring parasympathetic and sympathetic activity for the early identification of mortality and morbidity of severely or injured patients who may need alternate therapy to promote survival.

* * * * *